United States Patent [19]

Shukla et al.

[11] Patent Number: 5,962,003
[45] Date of Patent: Oct. 5, 1999

[54] PROCESS FOR THE PREPARATION OF POLYURETHANE MICROCAPSULES CONTAINING MONOCROTOPHOS

[75] Inventors: Parshuram Gajanan Shukla; Swaminathan Sivaram, both of Maharashtra; Natarajan Rajagopalan, Madras, all of India

[73] Assignee: Council of Scientific & Industrial Research, New Delhi, India

[21] Appl. No.: 09/050,797

[22] Filed: Mar. 30, 1998

[51] Int. Cl.$^6$ .................................................. A01N 25/28
[52] U.S. Cl. .......................... 424/406; 424/408; 514/119; 264/4.7; 427/212
[58] Field of Search .................................. 264/4.3–4.33, 264/4.7; 427/212, 213.3, 213.31, 213.33, 213.34; 424/405, 406, 408, 417, 419, 420; 514/119

[56] References Cited

U.S. PATENT DOCUMENTS

| | | | |
|---|---|---|---|
| 3,577,515 | 5/1971 | Uandegaer | 264/4.7 |
| 3,726,804 | 4/1973 | Matsukawa et al. | 264/4.7 |
| 4,076,774 | 2/1978 | Short | 264/4 |
| 5,603,986 | 2/1997 | Yabuuchi et al. | 427/213.34 |

OTHER PUBLICATIONS

DE1936748 Abstract of CAPLUS 72:91372, Jan. 1970.

*Primary Examiner*—Neil S. Levy
*Attorney, Agent, or Firm*—Abelman, Frayne & Schwab

[57] ABSTRACT

The present invention relates to a process for the preparation of polyurethane microcapsules containing monocrotophos, which comprises of preparing a solution of diol or polyol having a molecular weight in the range of 200–2000, crosslinker, monocrotophos and a catalyst selected from amino or organometallic compounds; dispersing this solution into a dilute solution of stabilizer which consists of a block copolymer having the general formula $[A]_n-[B]_m$ where A and B are chemically and compositionally dissimilar segments where n and m segments are in between 30–115 and 10–60 units respectively, such that the sum of n and m does not exceed 175 units, in an aliphatic hydrocarbon; adding an isocyanate dropwise to this dispersion; agitating the mixture at 1000–1400 revolutions per minute for the first 6–8 hours and then at 500–800 revolutions per minute for an additional period of 14–18 hours at a temperature between 30° to 40° C. to permit the formation of polyurethane microcapsules; heating the dispersion for an additional period of 1–2 hours at a temperature not exceeding 50° C.; filtering the microcapsules; washing the microcapsules with lower aliphatic hydrocarbon and drying the microspheres under vacuum at temperature between 20° to 35° C.

21 Claims, No Drawings

5,962,003

PROCESS FOR THE PREPARATION OF POLYURETHANE MICROCAPSULES CONTAINING MONOCROTOPHOS

FIELD OF THE INVENTION

The present invention relates to a process for the microencapsulation. The invention, particularly, relates to a process for the microencapsulation of a pesticide, especially monocrotophes (dimethyl (E)-1-methyl-2-(methylcarbamoyl) vinyl phosphate). The process involves using polyurethane as a wall material. Microcapsules or the microspheres which are obtained by the process of the present invention range in size from one micron to hundred microns.

PRIOR ART REFERENCES AND BACKGROUND OF THE INVENTION

Monocrotophos is both a systemic and contact pesticide, useful for a wide range of pests (Monocrotophos, In: The Pesticide Manual, ED. Worthing C. R. and Walker S. B., British Crop Protection Council, 1983, p 384). Pure monocrotophos is a colorless, crystalline material melting at 55° C. Technical monocrotophos having a purity of approximately 78% is semi solid to solid at room temperature. Monocrotophos is freely soluble in water and also in any organic solvents except aliphatic hydrocarbons. It is thermally unstable at temperature greater than 38° C. It decomposes in moist conditions and in the presence of short chain alcohols. It has acute oral lethal dose $(LD)_{50}$ (rat) 14 mg/kg and acute dermal $LD_{50}$ (rat) 336 mg/kg. Technical monocrotophos and its formulations like 40% and 25% solution come under WHO class 1B i.e. 'highly hazardous' class. Owing to its highly hazardous nature, there is a great need to encapsulate monocrotophos using a suitable polymer to reduce its oral toxicity. The present invention is, therefore, specifically pertains to a process for the preparation of polyurethane microcapsules containing monocrotophos.

Conventional pesticide formulations are generally available in the form of emulsifiable concentrate for foliar spray, granules for soil broadcast or wettable powder for seed-coat application. These conventional pesticide formulations, have certain drawbacks such as high mammalian toxicity, phytotoxicity and poor persistence due to environmental degradation which leads to its excessive applications. Therefore, a need exists for improving the formulation and application technology for existing pesticides in order to fulfill the needs of both the user and the environment.

Polymers have, traditionally, played an important role in agriculture (McCormick C. L., In: Encyclopedia of Polymer Science and Engineering, Vol. 1, $2^{nd}$ Ed., Wiley & Sons, New York, 1984). Various types of controlled release formulations of pesticides possessing many desirable properties have been reported (Controlled delivery of crop-protection agents, Taylor and Francis Ltd., London, Wilkins. R. M. Ed., 1990).

Microcapsule is one of the controlled release forms, wherein an active agent (core material) is surrounded by a polymer film. This is achieved by a process called microencapsulation. Different techniques of microencapsulation are known which include phase separation, interfacial polymerization and mechanical methods such as spray drying. Number of reviews on microencapsulation techniques have appeared in literature (i) Madan P. L., Asian J. Pharm. Sci., 9, 1979, p1; (ii) Thies C. In: Encyclopedia of Polymer Science and Engineering, Vol. 9, Wiley & Sons, New York, 1987, p 724 and (iii) Porte H. and Couarrze G., In: Hand book of Powder Technology, 9 (Powder Technology and Pharm. Processes) 1994, p 513). U.S. patents disclosing various microencapsulation methods have been consolidated (Gutcho M. 'Microcapsules and Microencapsulation Techniques', New York, Noyes Data, 1976).

Interfacial polymerization is an important method among the various microencapsulation techniques (Arshady R. J. Microencapsulation, 6(1), 1989, p1–12 and 13–28) especially for microencapsulation of pesticides since high active agent/polymer ratio (between 0.5 to 0.95) can be achieved. Microencapsulation by interfacial polymerization involves (i) preparation of an aqueous or organic solution of the active agent containing monomer A (ii) dispersion and emulsification of this solution in a continuous phase containing monomer B (iii) polymerization at the interface between A and B, resulting in the formation of membrane of polymer AB enclosing active agent and (iv) decantation, centrifugation or filtration of the microcapsules formed. Polymers employed in microencapsulation by interfacial polymerization include polyamide, polyester, polyurea and polyurethane.

Microencapsulation of water soluble active agents:

There are several methods described in literature for microencapsulation of water soluble active agents viz. solvent evaporation (Huang H. P. and Ghebre-Sellassie., J. Microencapsulation, 6, 1989, p 219; Tabato Y. and Langer R., Pharm Res., 10, 1993, p 391), phase separation (Max E. Sufdy, J. Appl. Poly Sci., 27, 1982, p 4753) and interfacial polymerization (kil-Yeong C., Kyoung S. M. and Taihyum C., Polymer (Korea), 15, 1991, p 548). The fine sprayable matrix particles of water soluble insecticidal carbamates produced by DuPont to give wettable powder formulations involve either co-precipitation or co-melting of pesticide and polymer (Tocker S., In: controlled Delivery of Crop Protection Agents, Ed. R. M. Wilkins, 1990, p 261).

As monocrotophos is unstable in aqueous medium, phase separation and interfacial polymerization (using water in oil system) method cannot be employed for preparation of microcapsules. Interfacial polymerization methods, reported so far, employ oil in water or water in oil systems. There does not exist any reported microencapsulation method by inter facial polymerization which involves oil in oil system. The phase separation technique can be employed without use of water. However, this technique needs solvents in large volumes. Furthermore, monocrotophos is unstable at temperature higher than 38° C. and readily reacts with amine. This severely limits the choice of polymer and available methods.

Although, microencapsulation using polyurethane as wall material is known in literature, it involves dispersion of organic phase consisting of isocyanate, glycol and active agent in an aqueous phase (i) Fuyuma H., shinjo G. and Tsuji K., J. Pesticide Sci., 9, 1984, p 511 (ii) Choi K.y., Min K. S., Park I. H., Kim K. S. and Chang T., Polymer (Korea), 14, 1990, p 392 (iii) Ohtsuti T., Polymer, 32, 1991, p 2395 (iv) JP 04, 76016 (v) Reddy P.V.S, Mahesh G. N. Ramesh S., Sivakumar P. A. and Radhakrishnan G., Macromolecular Reports, A32 (suppls. 5 & 6), 1995, p789 (v) JP 05, 194, 128 (CA 119:154041) (vi) JP 05, 201,814 (CA 119: 197763)). However, in view of the instability of monocrotophos in aqueous medium, the reported oil in water system described in above mentioned references is not applicable.

SUMMARY OF THE PRESENT INVENTION

As such, in order to overcome the drawbacks of the said prior art processes, the Applicants have now developed an improved process for the microencapsulation in which the entire process is conducted in two immiscible non aqueous phases at ambient temperatures.

OBJECTS OF THE INVENTION

The main object of the invention relates to a process for the microencapsulation in which the entire process is conducted in two immiscible non aqueous phases at ambient temperatures.

It is an additional object of the present invention to provide a process which employs only those reactants do not react chemically with monocrotophos.

Yet another aspect of the present invention provide a process to prepare polyurethane microcapsules of monocrotophos with relatively narrow particle size distribution in the range of 1–100 microns and preferably between 10–50 microns.

It is further object of the present invention to provide a process to prepare microcapsular formulation of monocrotophos which show very little release of monocrotophos in the first 6 to 12 hours after dilution with water.

DETAILED DESCRIPTION OF THE INVENTION

Accordingly, the present invention provides an improved process for the preparation of polyurethane microcapsules containing monocrotophos which comprises preparing a solution of diol or polyol having molecular weight in the range of 200–2000; crosslinker, monocrotophos and a catalyst selected from amino or organometallic compounds, dispersing this solution in a dilute solution of a stabilizer having the formula $[A]_n–[B]_m$ were A and B are chemically and compositionally dissimilar segments and where n and m segments are in between 30–115 and 10–60 units respectively and such that the sum of n and m does not exceed 175 units, and added in an aliphatic hydrocarbon, adding an isocyanate dropwise to the hydrocarbon, agitating the mixture at 1000–1400 revolutions per minute to the first 6–8 hours and then at 500–800 revolutions per minute for an additional period of 14–18 hours at a temperature between 30° to 40° C. to permit the formation of polyurethane microcapsules, heating the dispersion for an additional period of 1–2 hours at a temperature not exceeding 50° C., filtering the microcapsules, washing the microcapsules with lower aliphatic hydrocarbon and drying the microcapsules under vacuum at temperature between 20° to 35° C.

The diols suitable for use in the present invention are ethyleneglycol, diethylene glycol, propylene glycol, 1,4-butane diol, 1,4 hexane diol, dipropylene glycol, cyclohexyl 1,4 dimethanol, 1,8 octane diol and polyols such as poly (ethylene glycols), poly (propylene glycols), poly (tetramethylene glycols).

The preferred crosslinkers are, for example, trimethylol propane, glycerol hexane triols and pentaerythrytol.

Catalysts suitable for use in the invention are, for example, N,N-dimethylaminoethanol, N,N-dimethylcyclohexylamine, bis-(2-dimethylaminoethyl) ether, N,N dimethylacetylamine, Diaminobicyclooctane, stannous octoate and dibutyltin dilaurate. The concentration of catalyst is between 0.1 to 0.3 wt. % based on diol.

Yet another important feature of the present invention is the choice of the stabilizers which consist of block copolymers with general formula $[A]_n–[B]_m$ and are prepared by sequential anionic polymerization of monomer A followed by monomer B using methods described in prior art (Walbridge D. J., Chapter 3, In: Dispersion polymerization in organic medium, Ed. Barret K. E. J., John Wiley & Sons, 1975) Block copolymers thus prepared have a average molecular weight in the range of 2000 to 10000 and poly-dispersities as derived by the ratio of weight average molecular weight to average molecular weight less than 1.1. Typically block A comprises of segments of a diene or olefin polymer such as poly (butadiene), poly (isoprene), poly (ethylene) and poly (ethylene-co-propylene). Block B comprises segments of a polymer derived from ethylene oxide and/or propylene oxide such as poly (ethylene oxide), poly (propylene oxide) and poly (ethyleneoxide-co-propylene oxide).

The solvents suitable for use in the invention are aliphatic hydrocarbons of the general formula $C_nH_{2n+2}$ where n can be between 6–16. Examples are hexane, octane, decane, isooctane, dodecane, hexadecane, superior kerosene, paraffin oil, white mineral oil, molex raffinate or suitable mixtures thereof.

The isocyanates suitable for use in the invention are toluenediisocyanate, methylene diisocyanate, isophorone diisocyanante, cyclohexane-1–4, diiscoyanate, hexamethylene diisocyanate, m-tetramethyloxylene diisocyanate, 2,2,4- and 2,4,4-trimethyl hexamethylene diisocyanate and 2,5-norbornane diisocyanate.

Typically, the equivalent ratio of isocyanate to diol is maintained between 1 to 1.4, preferably, between 1.1 to 1.2. The amount of monocrotophos used is between 30 to 85 wt % based on total amount of diol and isocyanate taken. The amount of crosslinker used is between 5 to 50 wt % based on diol, the preferred amount being 10 to 40 wt %. The stabilizer is added as a solution in hydrocarbon, the concentration being in the range of 0.05 to 0.2 wt %. The total quantity of stabilizer varies between 0.5 to 3 wt % based on diol, the preferred quantity is between 1.1 to 1.9 wt % based on the diol. The ratio of the hydrocarbon solvent and diol is maintained between 10 to 30, the preferred ratio being 15 to 25. The fumed silica added in the present process ranges from 0.2 g to 0.4 g.

The reaction is conducted in a suitable apparatus with arrangement for efficient agitation. The agitator speed being not less than 1000 revolutions per minute. The mixture of isocyanate and aliphatic hydrocarbon is fed slowly into the reactor containing dispersion of diol, monocrotophos, crosslinker and catalyst at the rate of 0.5 to 1 ml per minute.

The reaction temperature is maintained between 25 to 60° C., preferably between 35–50° C. The reaction time is typically between 15–30 hours. The reaction mixture progressively turns opaque as the microdroplets coalesce to form hard microcapsules. At the end of the reaction, the microcapsules of polyurethane containing monocrotophos are decanted, washed thoroughly with hexane and dried under vacuum. The yields are typically in the range of 80 to 85 wt % based on the total weight of diol, isocyanate, monocrotophos and crosslinker charged. The microcapsules have a particle size in the range of 5 to 120 micron. Microcapsules are stored in paraffin oil as dispersion such that microcapsules content in oil is in the range of 50–70 wt %. Particle size can be controlled within more narrower limits by appropriate choice of the stabilizer, its concentration and agitator speed.

This invention is further illustrated by the following examples which should not be construed to limit the scope of the invention.

EXAMPLE 1

A solution is prepared by dissolving 0.0052 g diaminobicyclooctane, 1.20 g trimethylolpropane 9.7 g of monocrotophos and 3.0 g of diethylene glycol by heating the mixture at 50° C. for 10 minutes.

The stabilizer (50 mg), namely, a block copolymer of butadiene with ethylene oxide wherein the ratio of number average molecular weight of butadiene segment to ethylene oxide segments is 2.5 is dissolved in 10 g of paraffin oil.

A mixture of 8.7 g toluene diisocyanate with 7.3 g of paraffin oil is prepared;

5 g solution of the stabilizer in paraffin oil is placed in a vessel having a volume of approximately 250 mL and is further diluted by addition of 45 g of paraffin oil. The solution is brought to 35° C. and agitated using a turbine type stirrer at a speed of 1200 revolutions per minute. The solution of diol, crosslinker, monocrotophos and catalyst is added. After 15 minutes when emulsion of required droplet size is formed, a mixture of toluene diisocynate and paraffin oil (8 g) is added dropwise over a period of 15 minutes. This is followed by addition of 2.5 g solution of stabilizer in paraffin oil. Remaining quantity (8 g) of toluene diisocyanate and paraffin oil is added in a similar way as described above followed by addition of 2.5 g solution of stabilizer in paraffin oil.

After a period of 8 hours speed is reduced to 700 revolution per minute. Thereafter by stirring the mixture for further 15 hours, the temperature of the mixture is increased to 50° C. After stirring the mixture at 50° C. for 1 hour, 0.4 g of fumed silica is added. The temperature is lowered to 35° C. and 40 mL hexane is added. The mixture is then stirred for 10 minutes at 300 revolutions per minute.

The polyurethane microspheres are isolated by filtering the mixture, washing with hexane and drying under vacuum at 25° C. for 3 hours.

The yield of the product is 21.0 g. The spherical particles have a particle size in the range of 5–80 microns of which a majority of particles are 10–50 microns. To these microcapsules 10 g paraffin oil is added and are stored as dispersion.

EXAMPLE 2

A solution is prepared by dissolving 0.0042 g diaminobicyclootane, 0.6 g trimethylolpropane and 6.0 g of monocrotophos and 3.0 g of diethylene glycol by heating the mixture at 50° C. for 10 minutes.

The stabilizer (50 mg), namely, a block copolymer of butadiene with ethylene oxide wherein the ratio of number average molecular weight of butadiene segment to ethylene oxide segments is 2.5 is dissolved in 10 g of paraffin oil.

A mixture of 7.3 g toluene diisocyanate with 6.7 g of paraffin oil is prepared.

5 g solution of stabilizer in paraffin oil is placed in a vessel having a volume of approximately 250 mL and is further diluted by addition of 45 g of paraffin oil. The solution is brought to 35° C. and agitated using a turbine type stirrer at a speed of 1200 revolutions per minute. The solution of diol, crosslinker, monocrotophos and catalyst is added. After 15 minutes when emulsion of required droplet sized is formed, a mixture of toluene diisocyanate and paraffin oil (7 g) is added dropwise over a period of 12 minutes. This is followed by addition of 2.5 g solution of stabilizer in paraffin oil. Remaining quantity (7.0 g) of toluene diisocynate and paraffin oil is added in a similar way as described above followed by addition of 2.5 g solution of stabilize in paraffin oil.

After a period of 7 hours speed is reduced to 700 revolution per minute. Thereafter by stirring the mixture for further 15 hours, the temperature of the mixture is increased to 50° C. After stirring the mixture at 50° C. for 1 hour, 0.4 g of fumed silica is added. The temperature is lowered to 35° C. and 40 mL hexane is added. The mixture is then stirred for 10 minutes at 300 revolutions per minute.

The polyurethane microcapsules are isolated by filtering the mixture, washing with hexane and drying under vacuum at 25° C. for 3 hours.

The yield of the product is 15.0 g. The spherical particles have a particle size in the range of 5–80 microns of which a majority of particles are 10–50 microns. To these microcapsules 10 g paraffin oil is added and are stored as dispersion.

EXAMPLE 3

A solution is prepared by dissolving 0.0052 g diaminobicyclooctane, 0.3 g trimethylolpropane, 60 g of monocrotophos and 3.0 g of ethylene glycol by heating the mixture at 50° C. for 10 minutes.

The stabilizer (50 mg), namely, a block copolymer of butadiene with ethylene oxide wherein the ratio of number average molecular weight of butadiene segment to ethylene oxide segment is 2.5 is dissolved in 10 g of paraffin oil. The ratio of the hydrocarbon solvent to diol is maintained between 10–30, preferred ratio being 15–25.

10.8 g Toluene diisocyanate with 10 g of paraffin oil. 5 g solution of the stabilizer in paraffin oil is placed in a vessel having a volume of approximately 250 mL and is further diluted by addition of 45 g of paraffin oil. The solution is brought to 35° C. and agitated using a turbine type stirrer at a speed of 1200 revolutions per minute. The solution of diol, crosslinker, monocrotophos and catalyst is added. After 15 minutes when emulsion of required droplet size if formed, a mixture of toluene diisocyanate and paraffin oil (10.8 g) is added dropwise over a period of 18 minutes. This is followed by addition of 2.5 g solution of stabilizer in paraffin oil. Remaining quantity (10.0 g) of toluene diisocyanate and paraffin oil is added in a similar way as described above followed by addition of 2.5 g solution of stablizer in paraffin oil.

After a period of 7 hours speed is reduced to 700 revolution per minute. Thereafter by stirring the mixture for further 15 hours. The temperature of the mixture is increased to 50° C. After stirring the mixture at 50° C. for 1 hour, 0.4 g of fumed silica is added. The temperature is lowered to 35° C. and 40 mL hexane is added. The mixture is then stirred for 10 minutes at 300 revolutions per minute.

The polyurethane microspheres are isolated by filtering the mixture, washing with hexane and drying under vacuum at 25° C. for 3 hours.

The yield of the product is 18.0 g. The spherical particles have a particle size in the range of 5–80 microns of which a majority of particles are 10–50 microns. To these microcapsules 10 g paraffin oil is added and are stored as dispersion.

Characterization of polyurethane microcapsules of monocrotophos

For characterization of microcapsules, product from one of the above examples (example 3) is taken.

(2) Scanning Electron Microscopy (SEM):

The SEM of microcapsules containing monocrotophos and these from which monocrotophos has been extracted show that the product is a true microcapsule and not a microsphere.

(2) IR and $^{1}H$ NMR of monocrotophos:

IR and $^{1}H$ NMR spectra of monocrotophos and monocrotophos extracted from the microcapsules after refluxing with methylene chloride indicated that microtophos does not undergo any chemical reaction or degradation during the process of encapsulation.

(3) Release of monocrotophose from microcapsules:

To demonstrate the object of no release of monocrotophos in the initial period of 6–12 hours, the following experiment is carried out with microcapsular dispersion paraffin oil.

0.45 g sample of paraffin oil containing 60% microcapsules is weight accurately in 30 mL glass sample bottle with screw type cap and 20 mL distilled water is added. The bottle is kept in a shaking water bath at 30° C. After 6 hours the solution is filtered through G3 sintered crucible into a 250 mL conical flask. The bottle is gently rinsed with 2 mL of distilled water. The filtrate is then transferred into a 100 mL volumetric flask. The contents of the conical flask is rinsed with 25 mL of distilled water and transferred to a 100 mL volumetric flask. To this solution 13 mL of acetonitrile is added and the solution is diluted with distilled water upto the mark and analyzed by HPLC. The results indicate only 0.6 wt. % release of monocrotophos.

We claim:

1. A process which is conducted in two immiscible non-aqueous phases, for the preparation of polyurethane microcapsules containing monocrotophos which comprises preparing a solution by mixing a diol or a polyol having a molecular weight in the range of 200–2000, with a crosslinker, monocrotophos and a catalyst selected from amino or organometallic compounds; dispersing this solution into a dilute solution of a stabilizer which consists of a block copolymer having the general formula $[A]_n-[B]_m$ where A and B are chemically and compositionally dissimlar segments and where segments n and m are between 30–115 and 10–60 units, respectively, such that the sum of n and m does not exceed 175 units, in an aliphatic hydrocarbon; adding an isocyanate dropwise to this dispersion; agitating the mixture at 1000–1400 revolutions per minute for the first 6–8 hours and then at 500–800 revolutions per minute for an additional period of 14–18 hours at a temperature between 30° to 40° C. to permit the formation of polyurethane microcapsules; heating the dispersion for an additional period of 1–2 hours at a temperature not exceeding 50° C.; filtering the microcapsules; washing the microcapsules with a lower aliphatic hydrocarbon and drying the microcapsules under vacuum at a temperature between 20° to 35° C.

2. A process as claimed in claim 1 wherein fumed silica is added in an amount ranging between 0.2 g to 0.4 g.

3. A process as claimed in claim 1 wherein the non-polar aliphatic hydrocarbon solvent is selected from the group consisting of hexane, octane, decane, isoctane, dodecane, hexadecane, superior kerosene, paraffin oil, white mineral oil and molex raffinate.

4. A process as claimed in claim 1 wherein the reaction between isocyanate and diols or polyols is carried out in a temperature range of 25 to 60° C.

5. A process as claimed in claim 1 where the diol is selected from the group consisting of ethylene glycol, diethylene glycol, 1,4 butane diol and poly(tetramethylene glycol).

6. A process as claimed in claim 1 wherein the crosslinker is selected from the group consisting of trimethylol propane, glycerol and hexane triols, having a concentration between 5 to 50 wt % based on diol.

7. A process as claimed in claim 1 wherein the amount of crosslinker used is 5 to 50 wt % based on diol.

8. A process as claimed in claim 1 wherein the catalyst is selected from the group consisting of N,N-dimethylcyclohexylamine, N,N-dimethylcetylamine, diamino-bicyclooctane stannous octoate and dibutyltin dilaurate having a concentration between 0.1 to 0.3 wt % based on diol.

9. A process as claimed in claim 1 wherein the dispersion stabilizer is selected from the group consisting of block copolymers of butadiene and ethylene oxide, having a concentration between 0.5 to 3.0 wt % based on diol.

10. A process as claimed in claim 9 wherein the amount of stabilizer is between 1.1 to 1.9 wt % based on the diol.

11. A process as claimed in claim 1 wherein the isocyanate selected from the group consisting of toluene diisocyanate, methylene diisocyanate, isophorone diisocyanate and cyclohexane-1,4-diisocyanate.

12. A process as claimed in claim 1 wherein the ratio of hydrocarbon solvent to diol ranges between 10 to 30.

13. A process as claimed in claim 1 wherein the ratio of hydrocarbon solvent to diol is between 15 to 25.

14. A process as claimed in claim 1 wherein the quantity of monocrotophos that is encapsulated is 15–40 wt. % of the total microcapsule weight.

15. A process as claimed in claim 1 wherein the equivalent ratio of isocyanate to diol is 1 to 1.4.

16. A process as claimed in claim 1 wherein the isocyanate is added dropwise to the mixture of diol, crosslinker, catalyst, monocrotophos and dispersion stabilizer at the rate of 0.5 to 1.0 mL per minute.

17. A process as claimed in claim 1 wherein the polyurethane microcapsules of monocrotophos have a particle size in the range of 1–100 microns.

18. The process as claimed in claim 1 wherein the reaction between isocyanate and the diols and polyols is carried out at a temperature in the range of 30° to 55° C.

19. The process as claimed in claim 1 wherein the amount of crosslinker used is 10 to 40 wt. %, based on diol.

20. A process as claimed in claim 15 wherein the equivalent ratio of isocyanate to diol is between 1.1 to 1.2.

21. A process as claimed in claim 17 wherein the polyurethane microcapsules of monocrotophos have a particle size in the range of between 10 to 50 microns.

* * * * *